(12) United States Patent
Koullick et al.

(10) Patent No.: US 9,468,512 B2
(45) Date of Patent: Oct. 18, 2016

(54) IMPLANTS WITH ABSORBABLE AND NON-ABSORBABLE FEATURES FOR THE TREATMENT OF FEMALE PELVIC CONDITIONS

(75) Inventors: Edouard A. Koullick, Golden Valley, MN (US); Thomas Q. Dinh, Minnetonka, MN (US); Robert C. Grant, New Hope, MN (US)

(73) Assignee: Astora Women's Health, LLC, Eden Prairie, MN (US)

( * ) Notice: Subject to any disclaimer, the term of this patent is extended or adjusted under 35 U.S.C. 154(b) by 140 days.

(21) Appl. No.: 13/877,695

(22) PCT Filed: Oct. 6, 2011

(86) PCT No.: PCT/US2011/055092
§ 371 (c)(1),
(2), (4) Date: Apr. 4, 2013

(87) PCT Pub. No.: WO2012/048105
PCT Pub. Date: Apr. 12, 2012

(65) Prior Publication Data
US 2013/0197300 A1    Aug. 1, 2013

Related U.S. Application Data

(60) Provisional application No. 61/390,370, filed on Oct. 6, 2010.

(51) Int. Cl.
*A61F 2/02* (2006.01)
*A61F 2/00* (2006.01)
(Continued)

(52) U.S. Cl.
CPC ........... *A61F 2/0063* (2013.01); *A61F 2/0045* (2013.01); *A61L 31/048* (2013.01);
(Continued)

(58) Field of Classification Search
CPC .............. A61F 2/0045; A61F 2/0063; A61F 2210/0076; A61F 2250/0031; A61L 31/048; A61L 31/16; A61L 31/148; C08L 23/06
USPC ........ 600/37, 29–32; 128/834, 885, 897–899
See application file for complete search history.

(56) References Cited

U.S. PATENT DOCUMENTS

| 3,124,136 A | 3/1964 | Usher |
| 4,520,821 A | 6/1985 | Schmidt et al. |

(Continued)

FOREIGN PATENT DOCUMENTS

| AU | 2002241673 | 11/2005 |
| CA | 2404459 | 8/2005 |

(Continued)

OTHER PUBLICATIONS

Benderev, Theodore, "A Modified Percutaneous Outpatient Bladder Neck Suspension System," The J. of Urology, vol. 152, Dec. 1994, pp. 2316-2320.

(Continued)

*Primary Examiner* — Navin Natnithithadha
*Assistant Examiner* — Sunita Reddy
(74) *Attorney, Agent, or Firm* — Kagan Binder, PLLC (57) ABSTRACT

Described are methods, devices, and systems related to implants for the treatment of a female pelvic condition. The implants include absorbable and non-absorbable materials and can be introduced into the pelvic area transvaginally. Meshes of the invention provide benefits relating to improved tissue integration into the mesh, reduced infection likelihood, improved patient comfort following implantation, or combinations of thereof.

18 Claims, 1 Drawing Sheet

(51) Int. Cl.
*A61L 31/04* (2006.01)
*A61L 31/14* (2006.01)
*A61L 31/16* (2006.01)

(52) U.S. Cl.
CPC ............ *A61L 31/148* (2013.01); *A61L 31/16* (2013.01); *A61F 2210/0076* (2013.01); *A61F 2250/0031* (2013.01)

(56) References Cited

U.S. PATENT DOCUMENTS

| | | |
|---|---|---|
| 4,865,031 A | 9/1989 | O'Keeffe |
| 4,911,165 A | 3/1990 | Lennard et al. |
| 5,012,822 A | 5/1991 | Schwarz |
| 5,013,292 A | 5/1991 | Lemay |
| 5,032,508 A | 7/1991 | Naughton et al. |
| 5,036,867 A | 8/1991 | Biswas |
| 5,092,884 A | 3/1992 | Devereux et al. |
| 5,362,294 A | 11/1994 | Seitzinger |
| 5,393,594 A | 2/1995 | Koyfman et al. |
| 5,413,598 A | 5/1995 | Moreland |
| 5,628,756 A | 5/1997 | Barker, Jr. et al. |
| 5,795,584 A | 8/1998 | Totakura et al. |
| 5,919,232 A | 7/1999 | Chaffringeon et al. |
| 5,922,026 A | 7/1999 | Chin |
| 6,031,148 A | 2/2000 | Hayes et al. |
| 6,287,316 B1 | 9/2001 | Agarwal et al. |
| 6,306,079 B1 | 10/2001 | Trabucco |
| 6,334,446 B1 | 1/2002 | Beyar |
| 6,352,553 B1 | 3/2002 | van de Burg et al. |
| 6,482,214 B1 | 11/2002 | Sidor, Jr. et al. |
| 6,599,323 B2 | 7/2003 | Melican et al. |
| 6,612,977 B2 | 9/2003 | Staskin |
| 6,638,284 B1 | 10/2003 | Rousseau et al. |
| 6,648,921 B2 | 11/2003 | Anderson |
| 6,702,827 B1 | 3/2004 | Lund |
| 6,737,371 B1 | 5/2004 | Planck et al. |
| 6,755,781 B2 | 6/2004 | Gellman |
| 6,800,082 B2 | 10/2004 | Rousseau |
| 6,802,807 B2 | 10/2004 | Anderson |
| 6,884,212 B2 | 4/2005 | Thierfelder et al. |
| 6,911,003 B2 | 6/2005 | Anderson et al. |
| 6,953,428 B2 | 10/2005 | Gellman et al. |
| 6,971,986 B2 | 12/2005 | Staskin et al. |
| 6,981,944 B2 | 1/2006 | Jamiolkowski |
| 7,025,063 B2 | 4/2006 | Snitkin |
| 7,070,558 B2 | 7/2006 | Gellman et al. |
| 7,087,065 B2 | 8/2006 | Ulmsten et al. |
| 7,229,404 B2 | 6/2007 | Bouffier |
| 7,229,453 B2 | 6/2007 | Anderson |
| 7,268,205 B2 | 9/2007 | Williams et al. |
| 7,364,541 B2 | 4/2008 | Chu et al. |
| 7,407,480 B2 | 8/2008 | Staskin et al. |
| 7,513,865 B2 | 4/2009 | Bourne et al. |
| 7,527,588 B2 | 5/2009 | Zaddem et al. |
| 7,601,118 B2 | 10/2009 | Smith et al. |
| 7,611,454 B2 | 11/2009 | De Leval |
| 7,615,065 B2 | 11/2009 | Priewe et al. |
| 7,766,926 B2 | 8/2010 | Bosley et al. |
| 7,981,024 B2 | 7/2011 | Levy |
| 2002/0120291 A1 | 8/2002 | Shalaby |
| 2002/0147382 A1 | 10/2002 | Neisz et al. |
| 2002/0151909 A1 | 10/2002 | Gellman et al. |
| 2002/0161382 A1 | 10/2002 | Neisz |
| 2003/0004581 A1 | 1/2003 | Rousseau |
| 2003/0036676 A1 | 2/2003 | Scetbon |
| 2003/0065402 A1 | 4/2003 | Anderson et al. |
| 2003/0216814 A1* | 11/2003 | Siegel .................. A61F 2/0045 623/23.66 |
| 2004/0015057 A1 | 1/2004 | Rocheleau et al. |
| 2004/0054253 A1* | 3/2004 | Snitkin ............ A61B 17/00234 600/37 |
| 2004/0073235 A1 | 4/2004 | Lund |
| 2004/0225181 A1 | 11/2004 | Chu et al. |
| 2005/0038451 A1 | 2/2005 | Rao et al. |
| 2005/0283189 A1 | 12/2005 | Rosenblatt et al. |
| 2006/0089525 A1 | 4/2006 | Mamo et al. |
| 2007/0021826 A1* | 1/2007 | Case ..................... A61F 2/2418 623/1.15 |
| 2007/0219568 A1 | 9/2007 | Yeo et al. |
| 2007/0282160 A1 | 12/2007 | Sheu et al. |
| 2008/0039678 A1 | 2/2008 | Montpetit et al. |
| 2008/0081945 A1* | 4/2008 | Toso et al. ...................... 600/37 |
| 2008/0132602 A1 | 6/2008 | Rizk et al. |
| 2009/0156893 A1 | 6/2009 | Bourne et al. |
| 2009/0221868 A1 | 9/2009 | Evans |
| 2009/0312843 A1* | 12/2009 | Ford et al. .................. 623/23.72 |
| 2009/0318752 A1* | 12/2009 | Evans et al. .................... 600/37 |
| 2010/0189764 A1* | 7/2010 | Thomas et al. ............... 424/426 |
| 2010/0198002 A1* | 8/2010 | O'Donnell ............ A61F 2/0045 600/30 |
| 2010/0256442 A1* | 10/2010 | Ogdahl ................. A61F 2/0045 600/30 |
| 2010/0261950 A1 | 10/2010 | Lund |
| 2010/0261952 A1 | 10/2010 | Montpetit et al. |
| 2010/0261955 A1 | 10/2010 | O'Hern et al. |
| 2011/0034759 A1 | 2/2011 | Ogdahl et al. |
| 2011/0124954 A1 | 5/2011 | Ogdahl |
| 2011/0307077 A1* | 12/2011 | Pfeiffer ................. A61F 2/0045 623/23.72 |

FOREIGN PATENT DOCUMENTS

| | | |
|---|---|---|
| EP | 0248544 A1 | 12/1987 |
| EP | 0470308 A1 | 2/1992 |
| EP | 1060714 A3 | 9/2002 |
| GB | 2 222 954 A | 3/1990 |
| WO | WO9317635 A1 | 9/1993 |
| WO | WO 99/51163 | 10/1999 |
| WO | WO 00/16822 | 3/2000 |
| WO | WO0057812 A1 | 10/2000 |
| WO | WO0106951 A1 | 2/2001 |
| WO | WO 01/45588 | 6/2001 |
| WO | WO0139670 A1 | 6/2001 |
| WO | WO0156499 A1 | 8/2001 |
| WO | WO02071953 A2 | 9/2002 |
| WO | WO03003778 A1 | 4/2003 |
| WO | WO03028585 A2 | 4/2003 |
| WO | WO03037215 A2 | 5/2003 |
| WO | WO03041613 A1 | 5/2003 |
| WO | WO2005122954 A1 | 12/2005 |
| WO | WO 2006/116000 | 11/2006 |
| WO | WO2007011341 A1 | 1/2007 |
| WO | WO2007027592 A2 | 3/2007 |
| WO | WO 2010/088699 | 8/2010 |
| WO | WO 2011/063412 | 5/2011 |
| WO | WO 2011/072148 | 6/2011 |
| WO | WO 2012/050973 | 4/2012 |

OTHER PUBLICATIONS

Blaivas et. al., "Pubovaginal Fascial Sling for the Treatment of Complicated Stress Urinary Incontinence," The J. of Urology, vol. 145, Jun. 1991, pp. 1214-1218.

Burch, John C., "Urethrovaginal fixation to Cooper's ligament for correction of stress incontinence, cystocele, and prolapse," Am. J. Obstetrics and Gynecology, vol. 31, No. 2, Feb. 1961.

DeLancey, John, "Structural support of the urethra as it relates to stress urinary incontinence: the hammock hypothesis," Am. J. Obstetrics and Gynecology, vol. 170, No. 6, Jun. 1994, pp. 1713-1723.

Falconer et al., "Clinical outcome and changes in connective tissue metabolism after intravaginal slingplasty in stress incontinent women," Int. Urogynecol. J. (1996) 7:133-137.

Gilja et al., "A modifies raz bladder neck suspension operation (transvaginal burch)," The J. of Urology, vol. 153, 1455-1457, May 1995.

Hamilton et al., "Procedures for urinary incontinence in the United States, 1979-1997," Am. J. Obstet. Gynecol. vol. 189, No. 1, pp. 70-75 2003.

Handa et al., "Banked Human fascia lata for the suburethral sling procedure: a preliminary report," Obstetrics & Gynecology, vol. 88, No. 6, pp. 1045-1050, Dec. 1996.

(56) References Cited

OTHER PUBLICATIONS

Henriksson et al., "A urodynamic evaluation of the effects of abdominal urethrocystopexy and vaginal sling urethroplasty in women with stress incontinence," Am. J. Obstet. Gynecol., vol. 131, No. 1, pp. 77-83, May 1978.
Hodgkinson et al., "Urinary stress incontinence in the female: III. Round-ligament technic for retropubic suspension of the urethra," Obstetrics & Gynecology, vol. 10, No. 5 (1957).
Holschneider et al., "The modified pereyra procedure in recurrent stress urinary incontinence: a 15 year review," Obstetrics & Gynecology, vol. 83, No. 4 pp. 573-579 (1994).
Ingelman-Sundberg, "Surgical treatment of female urinary stress incontinence," Contr. Gynec. Obstet., vol. 10 pp. 51-69 (1983).
Klutke et al., "The anatomy of stress incontinence: magnetic resonance imaging of the female bladder neck and urethra," The J. or Urology, vol. 149, pp. 563-567 (1990).
Klutke et al., "Instruments & Methods: transvaginal bladder neck suspension to cooper's ligament: a modified pereyra procedure," Obstetrics & Gynecology, vol. 88, No. 2, pp. 293-297 (1996).
Leach et al., "Female stress urinary incontinence clinical guidelines panel summary report on surgical management of female stress urinary incontinence," Am. Urological Assc., vol. 158, 875-880 (1997).
Loughlin et al., "Review of an 8-year experience with modifications of endoscopic suspension of the bladder neck for female stress urinary incontinence," The Journal of Urology, vol. 143, pp. 3-4 (1990).
O'Donnell, Pat, "Combined Raz urethral suspension and McGuire pubovaginal sling for treatment of complicated stress urinary incontinence," The J. of the Ark. Med. Society, vol. 88, No. 8, pp. 389-392 (1992).
Parra. et al., "Experience with a simplified technique for the treatment of female stress urinary incontinence," British J. of Urology, vol. 68:615-617 (1990).
Pereyra, Armand, "A simplified surgical procedure for the correction of stress incontinence in women," West. J. Obst. & Gynec., Jul./Aug. 1959.
Petros et al., "Non stress non urge female urinary incontinence—diagnosis and cure: a preliminary report," Acta Obstet Gynecol Scand, 69 Suppl. 153:69-70 (1990).
Petros et al., "The role of a lax posterior vaginal fornix in the causation of stress and urgency symptoms: a preliminary report," Acta Obstet Gynecol Scand, 69 Suppl. 153:71-73 (1990).
Petros et al., "Bladder instability in women: a premature activation of the micturition reflex," Neurourology and Urodynamics, 12:235-239 (1993).
Petros et al., "Urethral pressure increase on effort originates from within the urethra, and continence from musculovaginal closure," Neurourology and Urodynamics, 14:337-350 (1995).
Petros et al., "An analysis of rapid pad testing and the history for the diagnosis of stress incontinence," Acta Obstet Gynecol Scand, 71:529-536 (1992).
Petros at al., "An integral theory of female urinary incontinence," Acta Obstet Gynecol Scand, 69 Suppl. 153:7-31 (1990).
Petros et al., "The tuck procedure: a simplified vaginal repair for treatment of female urinary incontinence," Acta Obstet Gynecol Scand, 69 Suppl. 153:41-42 (1990).
Petros et al., "Anchoring the midurethra restores bladder-neck anatomy and continence," The Lancet, vol. 354 (1999).
Petros et al., "The development of the intravaginal slingplasty procedure: IVS II (with bilateral tucks)," Scand. J. Urol. Nephrol. Suppl. No. 153:61-69 (1993).
Petros et al., "Part IV: Surgical applications of the theory—Development of the intravaginal sling plasty (IVS) procedure," Scand. J. Urol. Nephrol. Suppl. No. 153:53-57 (1993).
Petros et al., "An anatomical basis for success and failure of female incontinence surgery," Scand. J. Urol. Nephrol. Suppl. No. 153:55-61 (1993).
Petros et al., "Part II. The biomechanics of vaginal tissue and supporting ligaments with special relevance to the pathogenesis of female urinary incontinence," Scand. J. Urol. Nephrol. Suppl. No. 153:29-31 (1993).
Petros et al., "Further development of the intravaginal slingplasty procedure—IVS III (with midline tuck)," Scand. J. Urol. Nephrol. Suppl. No. 153:69-73 (1993).
Petros et al., "Part III. Surgical principles deriving from the theory," Scand. J. Urol. Nephrol. Suppl. No. 153:41-53 (1993).
Petros et al., "Part I. Theoretical, morphological, radiological correlations and clinical perspective," Scand. J. Urol. Nephrol. Suppl. No. 153:5-29 (1993).
Raz et al., "The Raz bladder neck suspension: results in 206 patients," The Journal of Urology, pp. 845-846 (1992).
Raz et al., "Modified bladder neck suspension for female stress incontinence," Urology, vol. XVII, No. 1, pp. 82-86 (1981).
Seim et al., "A study of female urinary incontinence in general practice," Scand. J. Urol. Nephrol 30;465-471 (1996).
Sloan et al., "Stress incontinence of urine: a retrospective study of the complications and late results of simple suprapubic suburethral fascial slings," The Journal of Urology, vol. 110, pp. 533-537 (1953).
Spencer et al., "A comparison of endoscopic suspension of the vesical neck with suprapubic vesicourethropexy for treatment of stress urinary incontinence," The Journal of Urology, vol. 137, pp. 411-416 (1987).
Stamey, Thomas, "Endoscopic suspension of the vesical neck for urinary incontinence in females," Am. Surg. pp. 465-472 (1980).
Stanton, Stuart, "Suprapubic approaches for stress incontinence in women," JAGS 38;348-351 (1990).
Studdiford, William, "Transplantation of abdominal fascia for the relief of urinary stress incontinence," Am. J. Obst & Gyne. vol. 47, pp. 764-776 (1994).
Ulmsten et al., "The unstable female urethra," Am. J. Obstet & Gynecol. vol. 144, No. 1 (1982).
Ulmsten et al., "Different biochemical composition of connective tissue in continent and stress incontinent women," Acta Obstet. Gynecol. Scand. 66:455-457 (1987).
Ulmsten et al., "Female urinary incontinence—a symptom, not a urodynamic disease. Some theoretical and practical aspect of the diagnosis a treatment of female urinary incontinence," Int. Urogynecology J. 6:2-3 (1995).
Ulmsten et al., "An ambulatory surgical procedure under local anesthesia for treatment of female urinary incontinence," Int. Urogynecology J. 7:81-86 (1996).
Ulmsten et al., "A multicenter study of tension-free vaginal tape (TVT) for surgical treatment of stress urinary incontinence," Int. Urogynecology J. 9:210-213 (1998).
Ulmsten et al., "A three-year follow up of tension free vaginal tape for surgical treatment of female stress urinary incontinence," British Journal of Obstetrics and Gynaecology, vol. 106 pp. 345-350 (1999).
Waxman et al., "Advanced urologic surgery for urinary incontinence," The female Patient, vol. 21, pp. 93-101 (1996).
Webster et al., "Voiding dysfunction following cystourethropexy: its evaluation and management," The Journal of Urology vol. 144, pp. 670-674 (1990).
Webster, George, "Female Urinary Incontinence," Urologic Surgery, 3rd Ed., pp. 665-680 (1983).
Winter, Chester, "Peripubic urethropexy for urinary stress incontinence in women," Urology, vol. XX No. 4, pp. 408-412 (1982).
Woodside et al., "Suprapubic endoscopic vesical neck suspension for the management of urinary incontinence in myelodysplastic girls," The Journal of Urology vol. 135, pp. 97-101 (1986).
Zacharin, Robert, "The suspensory mechanism of the female urethra," Journal of Anatomy, vol. 97, Part 3, pp. 423-430 (1963).
Zimmern et al., "Four-Corner bladder neck suspension," Vaginal Surgery for the Urologist, vol. 2, No. 1 pp. 29-37 (1994).
Jin-San Yoon et al., "Effects of poly(ethylene glycol)-*block*-poly(L-lactide) on the poly([R)3-hydroxybutyrate]/poly(L-lactide) blends," Elsevier, European Polymer Journal 36 (2000), pp. 435-442.
Arthrex DX Reinforcement Matrix Product Brochure, 2012.

\* cited by examiner

IMPLANTS WITH ABSORBABLE AND NON-ABSORBABLE FEATURES FOR THE TREATMENT OF FEMALE PELVIC CONDITIONS

PRIORITY

This application claims the benefit from International No. PCT/US2011/055092, which was granted an International Filing date of Oct. 6, 2011, which in turn claims the benefit of U.S. Provisional Patent Application Ser. No. 61/390,370, filed Oct. 6, 2010, entitled BIOABSORBABLE MESH FOR SURGICAL IMPLANTS, which applications are incorporated herein by reference in their entireties.

FIELD OF THE INVENTION

The present invention relates to implantable surgical meshes for the treatment of a female pelvic condition, and more particularly, to implantable surgical meshes that contain both absorbable and non-absorbable materials. The implantable surgical meshes are particularly useful for procedures involving a transvaginal insertion of all or part of the mesh to a target pelvic area.

BACKGROUND

Implantable surgical meshes have been widely used for a variety of different surgical procedures such as hernia repair, pelvic floor repair, urethral slings for treating fecal and urinary incontinence, and many others.

For example, urinary incontinence is a disorder that generally affects women of all ages. The inability to control urination can impact a subject both physiologically and psychologically. Urinary incontinence can interfere with a subject's daily activity and impair quality of life. Stress urinary incontinence is one type of urinary incontinence. Actions including straining, coughing, and heavy lifting can cause women with stress urinary incontinence to void urine involuntarily.

Various physiological conditions cause urinary incontinence in women. Stress urinary incontinence is generally caused by two conditions that occur independently or in combination. One condition, known as intrinsic sphincter deficiency (ISD), occurs when the urethral sphincter fails to coapt properly. ISD may cause urine to leak out of the urethra during stressful actions. A second condition, known as hypermobility, occurs when the pelvic floor is weakened or damaged and causes the bladder neck and proximal urethra to rotate and descend in response to increases in intra-abdominal pressure. When intra-abdominal pressure increases due to strain resulting from coughing, for example, urine leakage often results.

One method for treating stress urinary incontinence includes placing a sling to either compress the urethral sphincter or placing a sling to provide a "back stop" to the bladder neck and proximal urethra. Providing support to the bladder neck and proximal urethra maintains the urethra in the normal anatomical position, while elevation places the urethra above the normal anatomical position.

Other pelvic tissue disorders include cystocele, rectocele, enterocele, and prolapse such as vaginal vault prolapse. Pelvic disorders such as these can result from weakness or damage to normal pelvic support systems. Due to the lack of support, structures such as the uterus, bladder, urethra, small intestine, or vagina, may begin to fall out of their normal positions. Conditions referred to as "conditions of the pelvic floor" include conditions caused by weakness or injury to pelvic floor muscles, including levator muscles.

A cystocele is a medical condition that occurs when the tough fibrous wall between a woman's bladder and vagina (the pubocervical fascia) is weakened, such as by tearing, allowing the bladder to herniate into the vagina. A rectocele is a bulge of the front wall of the rectum into the vagina. The rectal wall may become thinned and weak, and it may balloon out into the vagina with pressure coming from the bowel. Enterocele is a hernia of the lining of the peritoneal cavity with or without abdominal viscera. The enterocele can occur posteriorly with or without inversion of the vagina.

Certain types of pelvic floor repair procedures, for example, can involve transvaginal access to internal tissue through a relatively small incision. Procedures can involve the transvaginal insertion of a support member, such as a mesh sling or implant, for supporting specific tissue. The support member may include a central tissue support portion positioned at tissue of a vaginal vault, and extension portions that are moved through respective tissue pathways and their ends anchored at target anatomical sites.

In a transvaginal procedure, portions of the implant are in contact with or pass through vaginal mucosal tissue, which is a unique anatomical area of the body and that presents some challenges for surgical procedures involving implanted meshes. The vaginal mucosa is lined by squamous epithelium without any glands, and the subepithelial layer contains the vaginal blood vessels. Vaginal secretions contain vaginal epithelial cells and Doderlein's bacilli. Doderlein's bacillus is a commensal species that lives in the vagina, and the bacillus metabolizes glycogen in the vaginal epithelial cells, producing lactic acid. This reduces the vaginal pH to around 5.0 with is too low for many other species including pathogens. Epithelial cells and bacillus that may become attached to the implant during or after the transvaginal procedure are of concerns following surgical implantation/fixation. For example, epithelialization of implant surfaces can prevent desirable tissue in-growth and healing around the mesh.

Accordingly, there is need for improved implantable surgical meshes that reduce or alleviate the problems associated with the treatment of female pelvic conditions.

BRIEF SUMMARY OF THE INVENTION

Generally, the invention relates to an implant comprising a mesh portion and configured for transvaginal implantation and positioning in the pelvic area, the implant including non-absorbable and absorbable materials. Embodiments of the invention provide benefits relating to improved tissue integration into the mesh, reduced infection likelihood, improved patient comfort following implantation, or combinations of thereof.

Implant embodiments of the current invention are configured for transvaginal insertion into a pelvic area of a female patient for the treatment of disorder or disease. The disorder or disease can be selected from, for example, urinary incontinence, vaginal prolapse, cystocele, and rectocele. Portions of the implant can have features to support an anatomical structure in the pelvis (i.e., a "support portion"), such as the vagina, bladder, urethra, or levator ani. Portions of the implant can also have features, such as straps or arms that extend from a support portion of the implant, or tissue anchors or fasteners (e.g., self-fixating tips), to help maintain the implant at a desired anatomical location in the pelvis.

In one embodiment, the invention provides an implant configured for transvaginal insertion into a female patient to treat a pelvic disorder. The implant comprises a first non-absorbable mesh layer, and a second absorbable layer. The second absorbable layer is non-porous or less porous than the first layer and prevents migration of cells through the second layer prior to its degradation in the body. Optionally, a bioactive agent can be associated with the second absorbable layer In a surgical procedure, the mesh can be implanted in the body using a step of transvaginally introducing all or a portion of the mesh into a target area in the female pelvic region. In the method, the implant having first non-absorbable and second absorbable layers is provided. An incision is made in the vaginal tissue, and then the mesh is transvaginally inserted into the patient so the second absorbable layer faces the incision site. For example, the mesh is implanted so the nonporous absorbable polymer layer faces the suture line when the original incision is closed. Following implantation, vaginal mucosa epithelial cells attach to the second absorbable layer, as the mesh is in contact with the vaginal tissue. The second absorbable layer prevents the rapid epithelialization of the first non-absorbable mesh layer by providing a barrier that degrades over time.

While epithelialization of the non-absorbable mesh (first layer) is being prevented by the second absorbable layer, tissue in-growth begins to fill the pores of the non-absorbable mesh and can eventually surround its structural features (e.g., filaments or molded cells) before the absorbable film becomes porous. The second absorbable layer can therefore reduce the exposure of small areas of mesh implants that otherwise may become apparent a few weeks or months following transvaginal implantation. In many cases these "early" exposures may otherwise occur at spots along the original incision line. Nonuniformities in wound closure may contribute to early mesh exposures. The barrier function provided by the second absorbable layer deters or prevents epithelialization that would otherwise hinder more desirable tissue ingrowth into the first non-absorbable mesh layer. After a period of time the second absorbable layer degrades and desirable tissue in growth occurs on the non-absorbable layer of the mesh.

In another embodiment, the mesh includes a biological reagent that has an effect on cellular material deposited from the vaginal mucosa on the implant surface when the implant is transvaginally inserted into the patient. Cells that can become deposed on the implant surface include mucosal epithelial cells and Doderlein's bacillus, and it can be desirable to affect these cells as they may be carried internally into the body from the vaginal mucosa during the transvaginal insertion. Alternatively, it can be desirable to affect internal tissue surrounding the implant after the transvaginal insertion of the implant.

Therefore, in another embodiment, the invention provides an implant configured for transvaginal insertion into a female patient to treat a pelvic disorder, wherein the implant includes a bioactive agent. The implant comprises a non-absorbable mesh, and an absorbable material, wherein absorbable material comprises a bioactive agent that is an antibiotic, antimicrobial, an inhibitor of epithelial cell activation and/or migration, or a compound that enhances wound regeneration. The absorbable material with bioactive agent is in the form of a coating on the non-absorbable mesh, an absorbable filament associated with the non-absorbable mesh, or a second layer associated with the non-absorbable mesh. The type and configuration of the bioabsorbable material associated with the implant can be chosen so any significant amount of bioactive agent is not prematurely released from the implant, an event which may otherwise have an undesirable affect on cells of the vaginal mucosa. Release occurs after implantation where the bioabsorbable material has time to degrade and release the bioactive agent to promote a desired biological effect. Optionally, a bioactive agent can be associated with the absorbable material which can optionally be present in the arms of the implant.

Another embodiment of the invention uses a combination of absorbable and non-absorbable materials to reduce or eliminate long-term post-implantation discomfort that may be experienced by a mesh recipient. Implantable meshes, such as those used in prolapse repair, can include a central mesh panel and "arms" that extend from the panel and pass through adjacent tissues to anchor the implant and provide support while tissue in-growth develops and matures in the central panel. In some meshes these anchoring arms pass through molded eyelets that enable the surgeon to adjust the position and tension applied to the central panel during implantation.

Therefore, in another embodiment, the invention provides an implant configured for transvaginal insertion into a female patient to treat a pelvic disorder, the implant comprising a central portion and two or more arms that extend from the central portion, wherein the central portion comprises a non-absorbable mesh, and the two or more arms comprise an absorbable material. Optionally, a bioactive agent can be associated with the absorbable material of the arms of the mesh implant. Following implantation, the arms are used to help secure or position the implant at a desired anatomical location in the pelvis. The arms provide this positioning support, but after a period of time, the bioabsorbable material in the arms degrades, thereby reducing the amount of synthetic material in the body and providing better long term comfort to the patient.

Use of absorbable material is also beneficial in that it can provide additional structural support to the non-absorbable mesh portion during an implantation step. This overcomes issues with some open weave or knit constructions that promote tissue in-growth after implantation but do not necessarily lend sufficient structural support to the mesh to aid in the process of implantation. Further, providing a closed-weave mesh that has sufficient structural support for implantation does not necessarily provide sufficient porosity to promote tissue in-growth for long term stability.

DETAILED DESCRIPTION OF THE INVENTION

All publications and patents mentioned herein are hereby incorporated by reference.

Implants of the invention are configured for transvaginal implantation and for female pelvic floor repair procedures. The implants can be used to treat a disorder or disease selected from, for example, urinary incontinence, vaginal prolapse, cystocele, and rectocele. As a general matter, the meshes include non-absorbable and absorbable materials. One part of the implant is a woven, knitted, or non-woven/non-knitted (e.g., molded) non-absorbable mesh (e.g., mesh layer). Bioabsorbable material can be associated with the implant in the form of fibers, a thin sheet or film, or a coating. The associated bioabsorbable material prior to absorption may lend additional structural support to the mesh for purposes of implantation. The implants can have sufficient rigidity for implantation, and in some constructions, sufficient openness in the weave pattern. The implant can be configured so the mesh is substantially open to promote tissue in-growth.

Embodiments of the implants of the invention include a mesh portion constructed from one or more nonabsorbable material(s). Exemplary nonabsorbable materials include synthetic polymers such as polyamides (e.g., nylons), fluoropolymers (e.g., polytetrafluoroethylene (PTFE) and polyvinylidene fluoride (PVF)), and polyolefins (e.g. polypropylene and polyethylene). In some aspects, polypropylene is used as a nonabsorbable material to form the mesh. Exemplary constructions use polypropylene, including isotactic and syndiotactic polypropylene, or blends thereof, to form the mesh. In some embodiments the implant has a knitted or woven construction using polypropylene monofilaments (see, for example, U.S. Pat. No. 4,911,165). The mesh can be constructed from a monofilament or a multifilament yarn.

In other embodiments the implant includes a non-knitted/non-woven (e.g., molded) polypropylene mesh layer (see, for example, commonly assigned PCT Publication Nos. WO2011/063412 and WO2011/072148). Non-knitted/non-woven meshes can be formed of patterned cells by way of a molding, die casting, laser etching, laser cutting, extruding, punching, or 3-D printing process. The portion of the implant that is the non-knitted/non-woven mesh can be considered a homogenous unitary construct. The pattern cut or formed implant can be constructed of a non-absorbable polymer material to provide a lattice support structure of repeated cells. Repeated cells or patterns in the implant generally form a lattice structure and can be cut or molded into sinusoid, or other waveform or undulating strut patterns to control elongation or compression along single or multiple axes to define a desirable pattern density with overall reduced surface area, and to control the distribution and shaping from applied loads. In some aspects the thickness of the non-absorbable mesh is in the range from about 0.005 inches to about 0.020 inches. In exemplary constructions, the mesh has a width in the range of about 5 mm to about 15 mm, and a length from about 6 cm to about 15 cm.

The implants of the invention also can include an "absorbable" material. The terms "bioabsorbable," "degradable," and "biodegradable," can also be used to describe a material that is absorbable, such as an absorbable polymer. Exemplary absorbable materials include polyhydroxyalkanoates, such as poly-4-hydroxybutyrate (P4HB), poly(3-hydroxyvalerate), polylactic acid, poly(lactide-co-glycolide), polycaprolactone, polyphosphazine, polyorthoesters, polyalkeneanhydrides, polyanhydrides, and polyesters, and the like. Polyhydroxyalkanoates include homopolymers such as poly-4-hydroxybutyrate (P4HB), poly(3-hydroxyvalerate), and hydroxyalkanoate copolymers such as poly(hydroxybutyrate-co-hydroxyvalerate) (Organ, S. J. (1994) Polymer, 35, 1:86-92) Blends of hydroxyalkanoate polymers with other absorbable polymers have also been prepared, such as poly($\beta$-hydroxybutyrate) and poly($\epsilon$-caprolactone) blends (Gassner, F., and Owen, A. J. (1994) Polymer, 35, 10:2233-2236).

Polyhydroxyalkanoate polymer compositions useful for preparing implants of the current invention are described in U.S. Pat. No. 7,268,205 (William et al.) and U.S. Pub No. 20080132602 (Rizk et al), the entireties of which is hereby incorporated by reference. Polyhydroxyalkanoate compositions, such as poly-4-hydroxybutyrate, can be manipulated using processing techniques such as solvent casting, melt processing, fiber processing/spinning/weaving, extrusion, injection and compression molding, and lamination, to prepare one or more portions of the implants of the current invention. Porous polyhydroxyalkanoate materials can be prepared by the addition of a salt to a molten polyhydroxyalkanoate composition, followed by subsequent removal of water to remove the salt to leave a porous structure. Degradation of the polyhydroxyalkanoate material can be increased by increasing the porosity of the material. In some aspects, the polyhydroxyalkanoate material of the mesh has an in vivo half-life of between three and six months or less.

Polyhydroxyalkanoate films can be prepared as described in U.S. Pub No. 20080132602 by solution casting techniques. Exemplary poly-4-hydroxybutyrate films having thicknesses of less than 10 mm, less than 1 mm, and less than 100 µm are described. If desired, cast films can be stretched and oriented uniaxially or biaxially to yield thinner and stronger films.

The polyhydroxyalkanoate can have a relatively low melting point/glass transition temperature, for example, less than 136° C. Polyhydroxyalkanoate polymers can also be soluble in a non-toxic, non-halogenated solvent, such as 1,4-dioxane or tetrahydrofuran (THF). In some aspects, bioactive agent-containing polyhydroxyalkanoate compositions can be prepared by including a drug that is soluble in the solvent used to dissolve the polyhydroxyalkanoate. Alternatively, small particulates of bioactive agent, not dissolvable in the polyhydroxyalkanoate solvent, can be homogenized in the polyhydroxyalkanoate solvent. Materials, such as fibers or sheets, can be formed from a melted polyhydroxyalkanoate composition, or a solvent-dissolved polyhydroxyalkanoate composition. In some embodiments of the invention, a solvent-dissolved polyhydroxyalkanoate composition can be used for coating all or a portion of the implant.

In some embodiments of the invention, a bioactive agent is associated with the implant. In exemplary arrangements, the absorbable material with the bioactive agent is in the form of an absorbable filament associated with the non-absorbable mesh, a second layer (e.g., a film or sheet) associated with the non-absorbable mesh layer, or a coating on the non-absorbable mesh.

Exemplary biologically-active components include: growth factors, pro-angiogenesis factors, anti-fibrotic agents, anti-microbial agents, antibiotics, immuno-suppressive agents, inhibitors of epithelial cell activation and/or migration, compounds that enhance wound regeneration, estrogen, other hormones, immunosupressants, anti-inflammatory agents, anti-cancer drugs, etc. For example, the bioactive agent can comprise the ovarian steroid, estrogen or Estradiol, to treat vaginal prolapse. The design of the mesh can be optimized to allow optimum initial mechanical properties of the mesh and optimum release profiles of the bioactive agents after implantation. The fibers may inherently and/or artificially comprise biologically-active components. In some embodiments, the invention provides an implant that treats pelvic organ prolapse, incontinence, or other urological disorders using the absorbable material to modulate release of the bioactive agent following transvaginal implantation.

In one embodiment, the implant can increase the thickness of the vaginal tube by the controlled release of estrogen and/or an ovarian steroid hormone from an implant used to treat prolapse. Additionally, the implant can allow for the remodeling of diseased tissues in order to prevent future recurrent prolapse. The implant embodiments of the invention can provide local and targeted delivery of a bioactive agent at low dosages, and therefore can circumvent issues associated with systemic therapies. The bioactive agent can be a simple formulation and, therefore, easy and inexpensive to manufacture.

The implant can deliver the bioactive agent locally to the desired location within the pelvic area in order to treat a pelvic disorder, while mechanically supporting the structure(s) affected by the pelvic disorder. The implant can controllably release the bioactive agent. The delivery device can degrade overtime, allowing the damaged tissues to remodel back into normal anatomical positions The bioactive agent can comprise any drug or combination thereof to treat a specific pelvic disorder. In one embodiment, the bioactive agent can comprise steroids. For example, the bioactive agent can comprise the ovarian steroid, estrogen, to treat vaginal prolapse.

In some embodiments, the implant comprises a mesh formed from a plurality of absorbable fibers and a plurality of non-absorbable fibers, the mesh further associated with a bioactive agent. For example, the mesh can include both non-absorbable and absorbable fibers that provide mechanical and bioactive agent-release properties. The fibers can be knitted, woven, or molded. The non-absorbable fibers can be made of polypropylene.

The absorbable fibers can be made of any biocompatible synthetic material, such as those described herein. An exemplary biocompatible synthetic material is that used in surgical sutures. A biological agent can be included in the absorbable fibers in an amount to provide a desired biological effect in the body following implantation. The eventual degradation of the absorbable fibers can provide for a less dense and lighter sling system.

Exemplary meshes include a plurality of absorbable fibers including an absorbable polyhydroxyalkanoate composition wherein the in vivo degradation rate of the fiber is controlled through the addition during manufacture of components to the polymeric composition, selection of the chemical composition, molecular weight, processing condition and form of the composition. A variety of knitted or woven patterns of the two fibers are also provided.

In exemplary meshes, a polypropylene non-absorbable fiber is knit or woven together with a polyhydroxyalkanoate absorbable fiber. The non-absorbable fibers can be paired with a polyhydroxyalkanoate absorbable fiber. The resulting paired fibers are then interwoven to form a bi-directional mesh structure prior to absorption of the absorbable fibers. In another exemplary construction, the polypropylene non-absorbable fibers can be aligned in a single direction along an X-axis while the plurality of absorbable fibers are interwoven with the non-absorbable filaments along the Y-axis to thereby form a bi-directional mesh structure prior to absorption of the absorbable fibers.

In another exemplary construction a polypropylene non-absorbable fiber is intermittently woven together with a polyhydroxyalkanoate absorbable fiber in an I-construction.

In another exemplary construction a polypropylene non-absorbable fiber is knit or woven together with a polyhydroxyalkanoate absorbable fiber to form a mesh sheet. The polypropylene non-absorbable fibers may be aligned in a single direction along an X-axis while the plurality of absorbable fibers may be interwoven with the non-absorbable filaments along the Y-axis. Alternatively, the plurality of absorbable fibers may be aligned in a single direction along the X-axis while the non-absorbable fibers are interwoven along the Y-axis. Polypropylene non-absorbable fibers and polyhydroxyalkanoate absorbable fibers may then run along an axis that is offset by about 45 degrees or more from the X and/or Y axes. Alternatively, the X and Y axis fibers may be the polypropylene non-absorbable fibers while the fibers running on the third axis may be exclusively polyhydroxyalkanoate absorbable fiber.

The meshes disclosed herein can be manufactured by any well known weaving or knitting techniques. For example, weaving can use a shuttle loom, Jacquard loom or Gripper loom. In these looms the process of weaving remains similar, the interlacing of two systems of yarns at right angles. This lacing can be simple as in a plain weave where the lacing is over one and under one. Placing the absorbable fibers in one direction, either fill or wrap will result in a final remaining product of the non-absorbent fibers running in one direction. Alternatively, the plain weave may be configured in a more elaborate construction such as twill weave or satin weave.

Another method of weaving is a leno weave. In this construction two warp yarns are twisted and the fill yarns are passed through the twist. In this type of weaving the warp yarns can be polypropylene while the fill yarn is polyhydroxyalkanoate fibers. Alternatively, for a more open construction the warp yarns can be polyhydroxyalkanoate while the fill yarn is polypropylene. Those skilled in the art will appreciate that additional variations of the basic weaves such as, sateen weaves, antique satin, warp faced twills, herringbone twills and the like can be used to create woven fabrics that will produce the same results when one of the directional yarns absorbs.

Other types of meshes can be constructed by knitting, which is a process of making cloth with a single yarn or set of yarns moving in only one direction. In weaving, two sets of yarns cross over and under each other. In knitting, the single yarn is looped through itself to make the chain of stitches. One method to do this is described as weft knitting. Knitting across the width of the fabric is called weft knitting.

Whether a woven or knit mesh is chosen, the ratio of absorbable to non-absorbable yarns can be adjusted. This will provide different amounts of structural integrity of the resulting mesh. For example, using pairs of non absorbable fibers and absorbable fibers would produce a final fabric, after absorption, with a larger open space between the non-absorbable fibers. Variations on this type construction will produce a remaining fabric, which promotes either more of less scar tissue depending on the amount of fabric and distance between sections. This can be adjusted for the type of tissue, which is being replaced. A lighter tissue, such as a fascia for supporting or connecting organs, can use a knitted mesh that has a wider section of absorbable and a narrower section of non-absorbable fibers.

A second method for knitting a fabric or mesh is warp knitting. In this method the fibers are introduced in the direction of the growth of the fabric (in the y direction). Warp knitting is a family of knitting methods in which the yarn zigzags along the length of the fabric, i.e., following adjacent columns ("wales") of knitting, rather than a single row ("course"). In this type of knitting the fibers are looped vertically and also to a limited extent diagonally, with the diagonal movement connecting the rows of loops. As with the weft knit fabrics, alternate yarns can be absorbable or non-absorbable. Controlling the number and ratio of absorbable to non-absorbable fibers will control the final material configuration and again the amount of tissue in-growth. Alternating absorbable and non-absorbable fibers produces a final construction with a narrow space between the remaining yarns which are filled in with tissue. As with woven fibers and meshes, the warp knits can be adjusted to create various amounts of tissue in-growth.

In another embodiment non-absorbable fibers, such as polypropylene fibers, are knit or woven together to form a mesh. The openings in the mesh are intermittently or completely filled with an absorbable material, such as a polyhydroxyalkanoate material. Depending on the initial degree of stiffness or rigidity that is required, a polyhydroxyalkanoate material may be used as a hot-melt glue intermittently at the intersecting portions of the polypropylene fibers. Alternatively the polyhydroxyalkanoate material may be used at all intersecting points. The absorbable composition that is filled into the openings in the mesh can also include a bioactive agent.

In this aspect, the absorbable material could be filled in so that it is present predominantly on one side of the mesh and forms a second, protective layer that shields the non-absorbable mesh from epithelial cell attachment following implantation. Alternatively, the absorbable material can be filled into the mesh so that it forms a glue for the attachment of a second, protective, absorbable layer. For example, the polyhydroxyalkanoate material can be coated on the polypropylene non-absorbable fibers to form a sheath, which, in addition to providing a barrier to epithelialization of the polypropylene mesh following implantation, functions as a cushion between the stiff polypropylene filaments and the tissue thereby reducing erosion problems.

Figure 1:
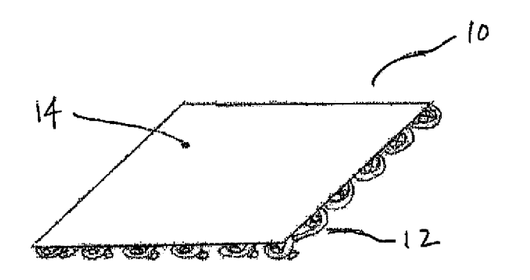
FIG. 1 is an illustration of an implant having non-absorbable and absorbable layers.

An implant with a first non-absorbable mesh layer, and a second absorbable layer that is non-porous or less porous than the first layer and prevents migration of cells through the second layer prior to its degradation in the body can be formed by attaching a thin absorbable film or sheet, such as formed by solvent casting herein, to a non-absorbable mesh. FIG. 1 illustrates such a mesh 10 showing a first non-absorbable layer 12, which can be prepared from a non-absorbable polymer, such as a polypropylene. One exemplary construction uses a molded polypropylene mesh layer. Another exemplary construction uses a nonabsorbable, large pore, monofilament, mesh. Preferably, the first layer has a thickness in the range of about 0.005 inches to about 0.020 inches, other preferred features or properties of the first absorbable layer are: porosity, flexibility/stiffness, etc.

The second absorbable layer 14, can be prepared from a single bioabsorbable polymer, such as a polyhydroxyalkanoate like hydroxybutyrate, or blend of bioabsorbable polymers. One exemplary construction uses a thin film of absorbable material prepared by solvent casting, such as described herein. Followings its introduction into the body, the second absorbable layer is impervious to cells, such as epithelial cells, from the vaginal incision site. After implantation, the second absorbable layer begins to erode and eventually allows cells to pass to the first non-absorbable layer. In some modes of practice, the second absorbable layer erodes and allows the passage of cells in a period of time in the range of about two weeks to about six months. However, in the time it takes for the second absorbable layer to erode and allow the passage of cells, non-epithelial cells and tissue healing components infiltrate the pores of the non-absorbable mesh layer and generate desirable tissue in-growth.

The first and second layers can be associated with each using one or more different techniques. In one exemplary construction, an absorbable adhesive is used to cause the first non-absorbable mesh layer to adhere to the second absorbable layer. For example, a hot melt adhesive including absorbable polymer can be used at selected points between the first and second layers. The adhesive can use either the same absorbable polymer as the second absorbable layer, or a different absorbable polymer formulation.

The implant can also include mechanical features to associate the first and second layers. For example, the second absorbable layer can be formed with regularly-spaced protruding features on one surface. These protruding features can be shaped and spaced to interact with the features of the first non absorbable mesh, such as large pore mesh features made using monofilaments. This type of attachment is therefore similar to that of conventional hook and loop fasteners.

The attachment feature (e.g, such as an adhesive or mechanical feature) can be formulated to absorb more rapidly in vivo than the second absorbable layer. This ensures substantial or complete tissue ingrowth in the first non-absorbable layer before fissures appear in the absorbable film layer. In some cases the second absorbable layer is formed from an absorbable homopolymer, and the attachment feature includes an absorbable copolymer that has a rate of degradation that is faster than the homopolymer. The homopolymer and copolymer can share a common monomer, such as a hydroxyalkanoate like hydroxybutyrate. Other copolymer types, for example, copolymers of ∊-caprolactone with dl-lactide have been synthesized to yield materials with rapid degradation rates.

In yet another embodiment, an apparatus for treating urinary incontinence in a female subject comprises a urethral sling having a central portion and first and second ends or arm. The first and second ends/arms are coupled to and extend from the central support portion. The central support portion is comprised of a mesh knit or woven from non-absorbable fibers or a non-woven/non-knitted (e.g., molded) mesh (and optionally including bioabsorbable material), while the first and second ends comprise absorbable material, such as absorbable fibers or an absorbable sheet. In some embodiments, the end portions comprise a mesh including bioabsorbable and non-absorbable fibers while the central portion comprises non-absorbable fibers. Following implantation, the arms are used to help secure or position the implant at a desired anatomical location in the pelvis. The arms provide this positioning support, but after a period of time, the bioabsorbable material in the arms degrades, thereby reducing the amount of synthetic material in the body and providing better long term comfort to the patient.

Implants of the invention can be part of a kit. The kit can include components for carrying out procedures for the insertion of the implant in a female patient. Exemplary components can include tissue fasteners, tools for introducing the implant into a female using a transvaginal insertion procedure, scalpels or knives for making the incision, and needles and suture material for closing the incision. All or parts of the kit can be sterilely packaged. Insertion tools useful for transvaginal insertion of the implant can include a handle and an elongate needle, wire, or rod extending from the handle. The needle, wire, or rod can be shaped (such as helical, straight, or curved) to be useful to carry the implant through a desired tissue path in the pelvic region.

The particular features of the implant embodiments of the invention can be adapted to known mesh implant constructions useful for treating female pelvic conditions, including those already described in the art. Those skilled in the art will recognize that various other mesh configurations, such as those described herein with reference to the following publications, can also be used in conjunction with the features and procedures of the current invention.

In some constructions, the implant is used for treating incontinence, prolapse, or a mixture of incontinence and prolapse, and includes a portion useful to support the urethra or bladder neck to address urinary incontinence, such as described in commonly assigned application published as US 2010/0256442 (Ogdahl, et al.), and exemplified by the mesh constructions of FIGS. 3B and 3C therein. The implant can be in the form of a mesh strip that in inserted transvaginally and used to support the urethra or bladder neck. The implant can be configured to have a length (distance between distal ends, e.g., self-fixating tips, of extension portions) to extend from a right obturator foramen to a left obturator foramen, (e.g., from one obturator internus muscle to the other obturator internus muscle). Exemplary lengths of an implant or implant portion for extension below the urethra, between opposing obturator foramen, from distal end to distal end of the extensions while laying flat, can be in the range from about 6 to 15 centimeters, e.g., from 7 to 10 centimeters or from 8 to 9 centimeters or about 8.5 centimeters. (Lengths L1 and L2 of FIGS. 3B and 3C can be within these ranges.) The lengths are for female urethral slings, and are for anterior portions of implants for treating female prolapse or combined female prolapse and incontinence, which include an anterior portion that has a length between ends of anterior extensions portions within these same ranges. A width of the extension portion can be as desired, such as within the range from about 1 to 1.5 centimeters. The implant can also have two or more tissue anchoring features (e.g., self-fixating tips). The self-fixating tips can be present at the ends of the mesh strips, or at the ends of arms or extensions that extend from a central support portion.

In some constructions, the mesh can be configured to treat pelvic conditions by supporting levator muscle, such as described in commonly assigned application published as US 2010/0261952 (Montpetit, et al.). The levator musculature or "levator ani" can include the puborectalis, pubococcygeus, iliococcygeus. Exemplary implants can be of a size and shape to conform to levator tissue, optionally to additionally contact or support other tissue of the pelvic region such as the anal sphincter, rectum, perineal body, etc. The implant can be of a single or multiple pieces that is or are shaped overall to match a portion of the levator, e.g., that is circular, oblong trapezoidal, rectangular, that contains a combination of straight, angled, and arcuate edges, etc. The implant can include attached or separate segments that fit together to extend beside or around pelvic features such as the rectum, anus, vagina, and the like, optionally to attach to the feature. The implant can include a tissue support portion, which at least in part contacts levator tissue. Optionally, the implant can additionally include one or more extension portion(s) that extends beyond the tissue support portion and to be secured to tissue of the pelvic region, for support of the tissue support portion. Optionally, extension portions can include features such as a tissue fastener (e.g., self-fixating tip, soft tissue anchor, bone anchor, etc.), a sheath, a tensioning mechanism such as a suture, an adjustment mechanism, etc.

According to exemplary methods, an implant for supporting levator muscle can be introduced through a vaginal incision that allows access to levator tissue. The method can include use of an insertion tool designed to reach through a vaginal incision, through an internal tissue path and to then extend through a second external incision. In some cases a tools is used to place a self-fixating tip at an internal location of the pelyic region, the tool length sufficient to reach from a vaginal incision to an obturator foramen, region of the ischial spine, sacrospinous ligament, or other location of placing a self-fixating tip. Exemplary methods include steps that involve creating a single medial transvaginal incision and dissecting within a plane or region of dissection including the ischorectal fossa. An implant can be inserted to contact tissue of the levator, over a desired area. A kit with the implant can include connectors for engagement between a needle of an insertion tool and a distal end of an extension portion, as well as helical, straight, and curved needles. An embodiment of a kit, including an insertion tool and an implant, is shown in FIG. 5 of US 2010/0261952.

The implant can include self-fixating tips designed to engage a distal end of an insertion tool to allow the insertion tool to place the self-fixating tip at a desired tissue location by pushing. For example, the mesh can be implanted by creating a single medial transvaginal incision under the mid-urethra, dissecting a tissue path on each side of the incision, passing a urinary incontinence sling through the incision whereby the urinary incontinence sling is suspended between the obturator internus muscles and the sling body is positioned between the patient's urethra and vaginal wall to provide support to the urethra. Commonly assigned application published as US 2011/0034759 (Ogdahl, et al.), also describes implants that include a self-fixating tip at a distal end of one or more extension portions, and transvaginal methods for inserting the mesh into a patient.

In some constructions, the mesh can be configured to treat vaginal prolapse, including anterior prolapse, posterior prolapse, or vault prolapse such as described in commonly assigned application published as US 2010/0261955-A1 (O'Hern, et al.). The mesh can be inserted transvaginally, following a single incision in the vaginal tissue, with no external incision. The mesh can be used to provide Level 1 support of the vaginal apex in combination with Level 2 support of medial vaginal sidewall tissue. In terms of vaginal prolapse, Level 1 vaginal tissue support relates to support of the top portion, or "apex" of the vagina. This section of tissue is naturally supported by the cardinal ligament that goes laterally to the ischial spine and crosses over medially to the sacrospinous ligament, and also by the uterosacral ligament that anchors into the sacrum. Level 2 support of vaginal tissue is support of tissue of the mid section of the vagina, below the bladder. This tissue is partially supported by the cardinal ligament but is predominantly supported by lateral fascial attachments to the arcus tendineus or white line. Level 3 support is that of the front end (sometimes referred to as the "distal" section) of the vagina right under the urethra. Natural support includes lateral fascial attachments that anchor into the obturator internus muscle.

The method for inserting the implant for treating vaginal prolapse can include providing an implant that includes a tissue support portion and two or more extension portions; placing the tissue support portion in contact with vaginal tissue to support the vaginal tissue; and extending a posterior extension portion to engage a sacrospinous ligament, and extending a lateral extension portion to engage tissue at a region of ischial spine, or extending a posterior extension portion to engage a sacrospinous ligament, and extending an anterior extension portion to engage an obturator foramen, or extending an extension portion to engage a sacrospinous ligament to provide Level 1 support, and supporting vaginal tissue to provide Level 2 support. FIG. 16 of US-2010-0261955-A1 illustrates a kit with an implant having a support portion piece, two extension portion pieces, adjusting tool, grommet management tool, and insertion tool.

In some modes of practice, the implants of the invention can be used along with an expansion member in a sacral colpopexy is a procedure for providing vaginal vault suspension, such as described in commonly assigned International Application No. PCT/US11/53985. A sacral colpopexy generally involves suspension, such as by use of a mesh strip implant, of the vaginal cuff to a region of sacral anatomy such as the sacrum (bone itself), a nearby sacrospinous ligament, uterosacral ligament, or anterior longitudinal ligament at the sacral promontory. The implant can be utilized in a transvaginal sacral colpopexy (TSCP) procedure with an expansion member to access tissue of the posterior pelvic region.

Implants can be prepared including a mesh that is low-density, bioactive, and image-capable. The low-density mesh relieves stress at the points of attachment. The bioactive mesh biologically treats and repairs the pelvic condition. The mesh can also be image-capable so that the implant can be visualized after implantation.

In some constructions, the non-absorbable fibers can comprise wire, allowing for the visualization of the implant after implantation. The wire can be made of fine tantalum and/or any other material known by a person skilled in the art and can be woven together with monofilaments of polypropylene or other polymers to create surgical meshes. In some constructions, the mesh can comprise radiopaque ink, allowing for the visualization of the entire mesh. The wire and/or radiopaque ink can provide imaging capability without extensive developmental work. Further, the wire and radiopaque ink do not substantially alter the mechanical properties of the existing mesh. Nor do the wire and radiopaque ink substantially alter local tissue response.

These and other features and advantages and embodiments of the present invention will become apparent from the following this description, when taken in conjunction with the accompanying drawing which illustrate, by way of example, the principles of the invention. It will be further apparent from the foregoing that other modifications of the inventions described herein can be made without departing from the spirit and scope of the invention.

What is claimed is:

1. An implant configured for transvaginal insertion into a female patient to treat a pelvic disorder, the implant comprising: a first non-absorbable mesh layer, a second absorbable layer comprising an absorbable hydroxyalkanoate polymer, wherein the second absorbable layer is non-porous and prevents migration of cells through the second layer prior to degradation of the second absorbable layer within the female patient, and an absorbable adhesive or protruding member comprising an absorbable polyester that is different than the hydroxyalkanoate polymer, that has a rate of degradation that is faster than the hydroxyalkanoate polymer, and which secures the first layer to the second layer, wherein the absorbable adhesive or the protruding member is formulated to absorb more rapidly in vivo than the second absorbable layer.

2. The implant of claim 1 wherein the first layer comprises a woven, knitted, or molded construction.

3. The implant of claim 1 wherein the first layer comprises polypropylene filaments or molded polypropylene.

4. The implant of claim 1 wherein the second layer has a side in contact with the first layer which comprises the protruding member configured to secure the first layer to the second layer.

5. The implant of claim 1 wherein the absorbable polyester is a polyester copolymer.

6. The implant of claim 1 wherein the first layer has a thickness in the range of 0.005 to 0.02 inches.

7. The implant of claim 1 wherein the second layer is a continuous film of absorbable material that is attached to the first non-absorbable mesh layer.

8. The implant of claim 1 wherein the second layer has a thickness in the range of 0.005 to 0.02 inches.

9. The implant of claim 1 wherein the second layer comprises a hydoxyalkanoate homopolymer.

10. The implant of claim 1 wherein the second layer comprises polyhydroxybutyrate.

11. The implant of claim 1 further comprising a bioactive agent.

12. The implant of claim 11 wherein the bioactive agent is selected from antibiotics, antimicrobials, inhibitors of epithelial cell activation and/or migration, and compounds that enhance wound regeneration selected from epidermal grown factor (EGF), transforming growth factor $\alpha$ or $\beta$ (TGF-$\alpha$ or $\beta$), vascular endothelial growth factor, platelet derived growth factor, and fibroblast growth factor.

13. The implant of claim 11 wherein the bioactive agent is present in the second absorbable layer and diffuses from the second absorbable layer or is released from the second absorbable layer upon degradation of absorbable material in the second absorbable layer.

14. The implant of claim 11 wherein the bioactive agent is present in a coating of absorbable material formed on the mesh of the first layer or the second layer.

15. The implant of claim 1 which is configured for the treatment of a pelvic disorder selected from urinary incontinence, vaginal prolapse, cystocele, and rectocele.

16. The implant of claim 1 further comprising a tissue anchor or fastener.

17. The implant of claim 1, the implant further comprising: a central portion and two or more arms that extend from the central portion, wherein the central portion comprises the first non-absorbable mesh layer, and the second absorbable layer, and the two or more arms comprise an absorbable material.

18. The implant of claim 1 wherein the absorbable polyester comprises one or more monomer(s) selected from the group consisting of hydroxyalkanoate, lactide, glycodlide, and caprolactone.

* * * * *